US008343907B2

(12) United States Patent
Bianchetti et al.

(10) Patent No.: US 8,343,907 B2

(45) Date of Patent: Jan. 1, 2013

(54) PARTICULATE BLEACHING COMPOSITION COMPRISING ENZYMES

(75) Inventors: Giulia Ottavia Bianchetti, Rome (IT); Gloria Dicapua, Rome (IT); Giovanni Grande, Rome (IT); Neil Joseph Lant, Newcastle upon Tyny (GB)

(73) Assignee: The Procter & Gamble Company, Cincinnati, OH (US)

(*) Notice: Subject to any disclaimer, the term of this patent is extended or adjusted under 35 U.S.C. 154(b) by 475 days.

(21) Appl. No.: 12/539,654

(22) Filed: Aug. 12, 2009

(65) Prior Publication Data

US 2010/0041579 A1 Feb. 18, 2010

(30) Foreign Application Priority Data

Aug. 13, 2008 (EP) .................................... 08162310

(51) Int. Cl.

*C11D 3/386* (2006.01)
*C11D 3/395* (2006.01)
*C12N 9/42* (2006.01)

(52) U.S. Cl. .................... 510/374; 252/186.43; 435/209

(58) Field of Classification Search .................. 510/374; 252/186.43; 435/209
See application file for complete search history.

(56) References Cited

U.S. PATENT DOCUMENTS

| | | | | |
|---|---|---|---|---|
| 3,812,044 | A | 5/1974 | Connor et al. | |
| 3,929,678 | A | 12/1975 | Laughlin et al. | |
| 4,105,827 | A | 8/1978 | Brichard et al. | |
| 4,179,390 | A | 12/1979 | Spadini et al. | |
| 4,228,044 | A | 10/1980 | Cambre | |
| 4,259,201 | A | 3/1981 | Cockrell et al. | |
| 4,536,314 | A | 8/1985 | Hardy et al. | |
| 4,704,233 | A | 11/1987 | Hartman et al. | |
| 4,762,433 | A | 8/1988 | Bergeson et al. | |
| 4,818,425 | A | 4/1989 | Meijer et al. | |
| 4,822,516 | A | 4/1989 | Suzuki et al. | |
| 4,945,053 | A | 7/1990 | Ito et al. | |
| 5,194,639 | A | 3/1993 | Connor et al. | |
| 7,033,981 | B2 | 4/2006 | Hakamada et al. | |
| 7,041,488 | B2 * | 5/2006 | Outtrup et al. | 435/209 |
| 7,141,403 | B2 | 11/2006 | Outtrup et al. | |
| 7,494,797 | B2 | 2/2009 | Mueller et al. | |
| 7,629,158 | B2 | 12/2009 | Perez-Prat Vinuesa et al. | |
| 2006/0035800 | A1 | 2/2006 | Gibson et al. | |
| 2007/0179076 | A1 | 8/2007 | Gibson et al. | |
| 2008/0005851 | A1 | 1/2008 | Perez-Prat Vinuesa et al. | |

FOREIGN PATENT DOCUMENTS

| | | |
|---|---|---|
| GB | 1082179 | 9/1967 |
| JP | 02047237 A | 2/1990 |
| WO | WO 92/06160 A1 | 4/1992 |
| WO | WO 00/41522 A2 | 7/2000 |

(Continued)

OTHER PUBLICATIONS

Blast2, alignment of instant SEQ ID No. 1 with SEQ ID No. 2 of Outtrup et al., NCBI Blast web site, Feb. 17, 2012, http://blast.ncbi.nlm.nih.gov/Blast.cgi?PAGE_TYPE=BlastSearch&PROG_DEF=blastn&BLAST_PROG_DEF=megaBlast&SHOW_DEFAULTS=on&BLAST_SPEC=blast2seq&LINK_LOC=align2seq).*

(Continued)

*Primary Examiner* — Rosanne Kosson

(74) *Attorney, Agent, or Firm* — Melissa G Krasovec; James F McBride

(57) ABSTRACT

Particulate bleach additive composition containing enzymes, which can be used to bleach fabrics in conjunction with a conventional granular or liquid laundry detergent.

14 Claims, 1 Drawing Sheet

AvO level is plotted versus time as follows to determine the total AvO in product.

FOREIGN PATENT DOCUMENTS

| | | | |
|---|---|---|---|
| WO | WO 2004074419 | A2 * | 9/2004 |
| WO | WO 2008/007318 | A2 | 1/2008 |

OTHER PUBLICATIONS

Boraston, A. B., et al., Carbohydrate-binding modules: fine-tuning polysaccharide recognition, Biochemical Journal, 2004, pp. 769-781, vol. 382 (part 3).
Bourne, Yves, et al., Glycoside hydrolases and glycosyltransferases: families and functional modules, Current Opinion in Structural Biology, 2001, pp. 593-600.
Boraston, A. B., et al., Identification and glucan-binding properties of a new carbohydrate-binding module family, Biochem. Journal, 2002, pp. 35-40, vol. 361.
Hakamada, Y., et al., Deduced Amino Acid Sequence and Possible Catalytic Residues of a Thermostable, Alkaline Cellulase from an Alkaliphilic *Bacillus* Strain, Biosci. Biotechnol. Biochem., 2000, pp. 2281-2289, vol. 64, No. 11.
Fukumori, F., et al., Molecular Cloning and Nucleotide Sequence of the Alkaline Cellulase Gene from the Alkalophilic *Bacillus* sp. Strain 1139, Journal of General Microbiology, 1986, pp. 2329-2335, vol. 132.
Sumitomo, N., et al., Nucleotide Sequence of the Gene for an Alkaline Endoglucanase from an Alkalophilic *Bacillus* and Its Expression in *Escherichia coli* and *Bacillus subtilis*, Biosci. Biotechnol. Biochem., 1992, pp. 872-877, vol. 56, No. 6.
International Search Report dated Aug. 13, 2009, containing 7 pages.

* cited by examiner

AvO level is plotted versus time as follows to determine the total AvO in product.
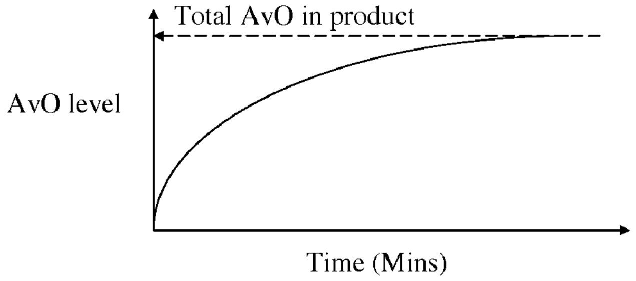

PARTICULATE BLEACHING COMPOSITION COMPRISING ENZYMES

CROSS REFERENCE TO RELATED APPLICATION

This application claims the benefit of EP Application No. 08162310.0 filed on Aug. 13, 2008.

FIELD OF THE INVENTION

The present invention relates to a particulate bleach additive composition containing enzymes, which can be used to bleach fabrics in conjunction with a conventional granular or liquid laundry detergent.

BACKGROUND OF THE INVENTION

Particulate bleaching compositions based on peroxygen oxygen bleaches suitable for the bleaching of stains on fabrics are based on so-called persalt bleaches such as sodium perborate, in its various hydrate forms, or on sodium percarbonate. Such persalt bleaches are sources of hydrogen peroxide when used in aqueous washing conditions. Nowadays, these compositions are very appreciated among consumers and there is a constant need to improve their performances. Particulate bleaching compositions contain thus more and more auxiliary ingredients, such as enzymes, which increase the performances of composition.

Cellulase enzymes have been used in detergent compositions for many years now for their known benefits of depilling, softness and colour care. However, the use of most of cellulases has been limited because of the negative impact that cellulase may have on the tensile strength of the fabrics' fibers by hydrolysing crystalline cellulose. Recently, cellulases with a high specificity towards amorphous cellulose have been developed to exploit the cleaning potential of cellulases while avoiding the negative tensile strength loss.

For example, Novozymes, in WO02/099091, discloses a novel enzyme exhibiting endo-beta-glucanase activity for use in detergent and textile applications. Novozymes further describes, in WO04/053039, detergent compositions comprising an endoglucanase and its combination with cellulases having increased stability towards anionic surfactant. Kao's EP 265832 describes novel alkaline cellulase. Kao further describes, in EP 1350843, alkaline cellulase which acts favourably in an alkaline environment.

However, it has always been difficult to formulate particulate bleach additive composition containing enzymes. It is, thus, an objective of the present invention to provide a particulate bleach additive composition comprising enzyme, which delivers effective bleaching performance on stained fabrics, when used in conjunction with a conventional particulate laundry detergent. The inventors have now found that the combination of some enzymes with particulate bleaching compositions, based on peroxygen oxygen bleaches, leads to a surprising improvement in cleaning and in whitening performance as well as on fabrics safety.

An advantage of the compositions of the present invention is, thus, that the particulate bleach additives herein are suitable for the bleaching of different types of fabrics including natural fabrics, (e.g., fabrics made of cotton, and linen), synthetic fabrics such as those made of polymeric fibres of synthetic origin (e.g., polyamide-elasthane) as well as those made of both natural and synthetic fibres. For example, the particulate bleach additives of the present invention herein may be used on synthetic fabrics despite a standing prejudice against using bleaches on synthetic fabrics, as evidenced by warnings on labels of clothes and commercially available bleaching compositions like hypochlorite-containing compositions. The compositions of the present invention have thus the benefit of having excellent cleaning performance while still being safe to fabrics.

Another advantage of the particulate bleach additives according to the present invention is that they can be used in a variety of conditions, i.e., in hard and soft water.

Yet another advantage of the compositions of the present invention is that they exhibit also effective stain removal performance on various stains including enzymatic stains and/or greasy stains.

By "bleach additives" it is meant herein, a particulate composition that is used in conjunction with, this means added to the washing machine together with, a conventional laundry detergent, in particular a particulate laundry detergent, in a laundry washing operation.

SUMMARY OF THE INVENTION

The present invention provides a composition comprising (a) from 5% to a 80% of an oxygen bleach or a mixture thereof, (b) from 0.01 to 20% of surfactants or a mixture thereof and, (c) from 0.00005% to 0.3% of an enzyme having the characteristics of: (i) exhibiting endo-beta-1,4-glucanase activity (E.C. 3.2.1.4); (ii) having greater than 80% of maximum activity at pH 9.2 when measured at 40° C.; and (iii) having a structure which does not comprise a Class A Carbohydrate Binding Module (CBM); and wherein the weight ratio of available oxygen to surfactant is greater than 0.45.

BRIEF DESCRIPTION OF THE FIGURE

The invention will be described in more detail below, in conjunction with the following FIGURE, in which:

FIG. 1 represents the AvO level as plotted versus time to determine the total AvO in product.

SEQUENCE LISTING

SEQ ID NO: 1 shows the amino acid sequence of an endoglucanase from *Bacillus* sp. AA349

SEQ ID NO: 2 shows the amino acid sequence of an endoglucanase from *Bacillus* sp KSM-S237

DETAILED DESCRIPTION OF THE INVENTION

The Particulate Bleach Additive Composition

The particulate bleaching compositions herein are so called particulate bleach additive compositions suitable for use in conjunction with a conventional laundry detergent, and in particular with particulate laundry detergents, to treat (stained) fabrics. The terms "additive" or "through-the-wash (bleaching) composition" refer to compositions that are preferably employed in the specific process of treating, preferably bleaching, fabrics as encompassed by the present invention.

Indeed, additive compositions are added together with a conventional laundry detergent (preferably particulate laundry detergent) into a washing machine and are active in the same wash-cycle. By contrast, so-called 'spotter' or 'pretreater' compositions that are applied, mostly undiluted, onto fabrics prior to washing or rinsing the fabrics and left to act thereon for an effective amount of time. Furthermore, so-called 'soakers' or 'rinse-added' compositions are contacted, mostly in diluted form, with fabrics prior or during rinsing of fabrics with water.

The bleach additive compositions herein are particulate compositions. By "particulate" it is meant herein powders, pearls, granules, tablets and the like. Particulate compositions are preferably applied onto the fabrics to be treated dissolved in, an appropriate solvent, typically water.

The particulate bleach additive composition herein have a pH measured at 25° C., preferably of at least, with increasing preference in the order given, 0.1, 0.5, 1, 1.5, 2, 2.5, 3, 3.5, 4, 4.5, 5, 5.5, 6, 6.5, 7, when diluted into 1 to 500 times its weight of water. Independently, particulate bleach additive composition herein have a pH measured at 25° C., preferably of no more than, with increasing preference in the order given, 12, 11.5, 11, 10.5, 10, 9.5, 9, 8.5 or 8, when diluted into 1 to 500 times its weight of water.

The compositions of the present invention are granular compositions. These compositions can be made by a variety of methods well known in the art, including dry-mixing, spray drying, agglomeration and granulation and combinations thereof. The compositions herein can be prepared with different bulk densities, from conventional granular products to so called "concentrated" products (i.e., with a bulk density above 600 g/l).

The Enzyme

As a first essential element of the present invention, the particulate bleaching compositions herein described comprises an enzyme. Preferably the enzyme is present in an amount comprised from 0.00005% to 0.3%, by weight of the total composition. More preferably, the enzyme will typically be comprised in the detergent composition at a level of from 0.00005% to 0.15%, from 0.0002% to 0.02%, or even from 0.0005% to 0.01% by weight of pure enzyme.

The enzyme of the present invention has the property of:

i. Exhibiting endo-beta-1,4-glucanase activity (E.C. 3.2.1.4); and ii. Exhibiting greater than 80% of maximum activity at pH 9.2 when measured at 40° C.; and iii. Comprising a structure which does not comprise a Class A Carbohydrate Binding Module (CBM).

Enzyme activity as a function of pH at 40° C. is measured using the protocol given in WO2002/099091, example 9, page 31.

A Class A CBM is defined according to A. B. Boraston et al. Biochemical Journal 2004, Volume 382 (part 3) pages 769-781. In particular, the cellulase does not comprise a Class A CBM from families 1, 2a, 3, 5 and 10.

Preferably the enzyme is an endoglucanase, more preferably the endoglucanase is a glycosyl hydrolase having enzymatic activity towards amorphous cellulose substrates, wherein the glycosyl hydrolase is selected from GH families 5, 7, 12, 16, 44 or 74. Preferably, the cellulase is a glycosyl hydrolase is selected from GH family 5.

More preferably, the endoglucanase is a polypeptide containing (i) at least one family 17 carbohydrate binding module (Family 17 CBM) and/or (ii) at least one family 28 carbohydrate binding module (Family 28 CBM). Please refer for example to: Current Opinion in Structural Biology, 2001, 593-600 by Y. Bourne and B. Henrissat in their article entitled: "Glycoside hydrolases and glycosyltransferases: families and functional modules" for the definition and classification of CBMs. Please refer further to Biochemical Journal, 2002, Volume 361, pages 35-40 by A. B. Boraston et al in their article entitled: "Identification and glucan-binding properties of a new carbohydrate-binding module family" for the properties of the family 17 and 28 CBM's.

Preferably, the composition according to the present invention comprises one or more bacterial alkaline enzyme(s) exhibiting endo-beta-1,4-glucanase activity (E.C. 3.2.1.4). The combination of the endoglucanase with the bleach catalyst significantly improves the cleaning and whitening performance while retaining good stability of the enzyme during storage and during the wash process.

As used herein the term "alkaline endoglucanase", shall mean an endoglucanase having an pH optimum above 7 and retaining greater than 70% of its optimal activity at pH 10. Preferably, the endoglucanase is a bacterial polypeptide endogenous to a member of the genus *Bacillus*.

In a more preferred embodiment, said enzyme comprises a polypeptide (or variant thereof) endogenous to one of the following *Bacillus* species:

| *Bacillus* sp. | As described in: |
|---|---|
| AA349 (DSM 12648) | WO 2002/099091A (Novozymes) p2, line 25<br>WO 2004/053039A (Novozymes) p3, line 19 |
| KSM S237 | EP 1350843A (Kao) p3, line 18 |
| 1139 | EP 1350843A (Kao) p3, line 22 |
| KSM 64 | EP 1350843A (Kao) p3, line 24 |
| KSM N131 | EP 1350843A (Kao) p3, line 25 |
| KSM 635, FERM BP 1485 | EP 265 832A (Kao) p7, line 45 |
| KSM 534, FERM BP 1508 | EP 0271044 A (Kao) p9, line 21 |
| KSM 539, FERM BP 1509 | EP 0271044 A (Kao) p9, line 22 |
| KSM 577, FERM BP 1510 | EP 0271044 A (Kao) p9, line 22 |
| KSM 521, FERM BP 1507 | EP 0271044 A (Kao) p9, line 19 |
| KSM 580, FERM BP 1511 | EP 0271044 A (Kao) p9, line 20 |
| KSM 588, FERM BP 1513 | EP 0271044 A (Kao) p9, line 23 |
| KSM 597, FERM BP 1514 | EP 0271044 A (Kao) p9, line 24 |
| KSM 522, FERM BP 1512 | EP 0271044 A (Kao) p9, line 20 |
| KSM 3445, FERM BP 1506 | EP 0271044 A (Kao) p10, line 3 |
| KSM 425. FERM BP 1505 | EP 0271044 A (Kao) p10, line 3 |

Suitable endoglucanases for the compositions of the present invention are:

1) An enzyme exhibiting endo-beta-1,4-glucanase activity (E.C. 3.2.1.4), which has a sequence of at least 90%, preferably 94%, more preferably 97% and even more preferably 99%, 100% identity to the amino acid sequence of position 1 to position 773 of SEQ ID NO:1 (Corresponding to SEQ ID NO:2 in WO02/099091); or a fragment thereof that has endo-beta-1,4-glucanase activity, when identity is determined by GAP provided in the GCG program using a GAP creation penalty of 3.0 and GAP extension penalty of 0.1. The enzyme and the corresponding method of production is described extensively in patent application WO02/099091 published by Novozymes A/S on Dec. 12, 2002. Please refer to the detailed description pages 4 to 17 and to the examples page 20 to page 26. One of such enzyme is commercially available under the tradename Celluclean™ by Novozymes A/S.

GCG refers to the sequence analysis software package provided by Accelrys, San Diego, Calif., USA. This incorporates a program called GAP which uses the algorithm of Needleman and Wunsch to find the alignment of two complete sequences that maximises the number of matches and minimises the number of gaps.

2) Also suitable are the endoglucanase enzymes described in EP 1 350 843A published by Kao corporation on Oct. 8, 2003. Please refer to the detailed description [0011] to [0039] and examples 1 to 4 [0067] to [0077] for a detailed description of the enzymes and its production. The alkaline endoglucanase variants are obtained by substituting the amino acid residue of a cellulase having an amino acid sequence exhibiting at least 90%, preferably 95%, more preferably 98% and even 100% identity with the amino acid sequence represented by SEQ. ID NO:2 (Corresponding to SEQ. ID NO:1 in EP 1 350 843 on pages 11-13) at (a) position 10, (b) position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564, or (p) position 608 in SEQ ID NO:2 or at a position corresponding thereto with another amino acid residue.

Examples of the endoglucanase having the amino acid sequence represented by SEQ. ID NO:2" include Eg1-237 [derived from *Bacillus* sp. strain KSM-S237 (FERM BP-7875), Hakamada, et al., Biosci. Biotechnol. Biochem., 64, 2281-2289, 2000]. Examples of the “alkaline cellulase having an amino acid sequence exhibiting at least 90% homology with the amino acid sequence represented by SEQ. ID NO:2” include alkaline cellulases having an amino acid sequence exhibiting preferably at least 95% homology, more preferably at least 98% homology, with the amino acid sequence represented by SEQ. ID NO:2. Specific examples include alkaline cellulase derived from *Bacillus* sp. strain 1139 (Eg1-1139) (Fukumori, et al., J. Gen. Microbiol., 132, 2329-2335) (91.4% homology), alkaline cellulases derived from *Bacillus* sp. strain KSM-64 (Eg1-64) (Sumitomo, et al., Biosci. Biotechnol. Biochem., 56, 872-877, 1992) (homology: 91.9%), and cellulase derived from *Bacillus* sp. strain KSM-N131 (Eg1-N131b) (Japanese Patent Application No. 2000-47237) (homology: 95.0%).

The amino acid is preferably substituted by: glutamine, alanine, proline or methionine, especially glutamine is preferred at position (a), asparagine or arginine, especially asparagine is preferred at position (b), proline is preferred at position (c), histidine is preferred at position (d), alanine, threonine or tyrosine, especially alanine is preferred at position (e), histidine, methionine, valine, threonine or alanine, especially histidine is preferred at position (f), isoleucine, leucine, serine or valine, especially isoleucine is preferred at position (g), alanine, phenylalanine, valine, serine, aspartic acid, glutamic acid, leucine, isoleucine, tyrosine, threonine, methionine or glycine, especially alanine, phenylalanine or serine is preferred at position (h), isoleucine, leucine, proline or valine, especially isoleucine is preferred at position (i), alanine, serine, glycine or valine, especially alanine is preferred at position (j), threonine, leucine, phenylalanine or arginine, especially threonine is preferred at position (k), leucine, alanine or serine, especially leucine is preferred at position (l), alanine, aspartic acid, glycine or lysine, especially alanine is preferred at position (m), methionine is preferred at position (n), valine, threonine or leucine, especially valine is preferred at position (o) and isoleucine or arginine, especially isoleucine is preferred at position (p).

The “amino acid residue at a position corresponding thereto” can be identified by comparing amino acid sequences by using known algorithm, for example, that of Lipman-Pearson’s method, and giving a maximum similarity score to the multiple regions of similarity in the amino acid sequence of each alkaline cellulase. The position of the homologous amino acid residue in the sequence of each cellulase can be determined, irrespective of insertion or depletion existing in the amino acid sequence, by aligning the amino acid sequence of the cellulase in such manner (FIG. 1 of EP 1 350 843). It is presumed that the homologous position exists at the three-dimensionally same position and it brings about similar effects with regard to a specific function of the target cellulase.

With regard to another endoglucanase having an amino acid sequence exhibiting at least 90% homology with SEQ. ID NO:2, specific examples of the positions corresponding to (a) position 10, (b), position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564 and (p) position 608 of the alkaline cellulase (Eg1-237) represented by SEQ. ID NO: 2 and amino acid residues at these positions will be shown below:

| | Egl-237 | Egl-1139 | Egl-64 | Egl-N131b |
|---|---|---|---|---|
| (a) | 10Leu | 10Leu | 10Leu | 10Leu |
| (b) | 16Ile | 16Ile | 16Ile | Nothing corresponding thereto |
| (c) | 22Ser | 22Ser | 22Ser | Nothing corresponding thereto |
| (d) | 33Asn | 33Asn | 33Asn | 19Asn |
| (e) | 39Phe | 39Phe | 39Phe | 25Phe |
| (f) | 76Ile | 76Ile | 76Ile | 62Ile |
| (g) | 109Met | 109Met | 109Met | 95Met |
| (h) | 242Gln | 242Gln | 242Gln | 228Gln |
| (i) | 263Phe | 263Phe | 263Phe | 249Phe |
| (j) | 308Thr | 308Thr | 308Thr | 294Thr |
| (k) | 462Asn | 461Asn | 461Asn | 448Asn |
| (l) | 466Lys | 465Lys | 465Lys | 452Lys |
| (m) | 468Val | 467Val | 467Val | 454Val |
| (n) | 552Ile | 550Ile | 550Ile | 538Ile |
| (o) | 564Ile | 562Ile | 562Ile | 550Ile |
| (p) | 608Ser | 606Ser | 606Ser | 594Ser |

3) Also suitable is the alkaline cellulase K described in EP 265 832A published by Kao on May 4, 1988. Please refer to the description page 4, line 35 to page 12, line 22 and examples 1 and 2 on page 19 for a detailed description of the enzyme and its production. The alkaline cellulase K has the following physical and chemical properties:

1. Activity: Having a Cx enzymatic activity of acting on carboxymethyl cellulose along with a weak $C_1$ enzymatic activity and a weak beta-glucoxidase activity;
2. Specificity on Substrates: Acting on carboxymethyl cellulose(CMC), crystalline cellulose, Avicell, cellobiose, and p-nitrophenyl cellobioside (PNPC);
3. Having a working pH in the range of 4 to 12 and an optimum pH in the range of 9 to 10;
4. Having stable pH values of 4.5 to 10.5 and 6.8 to 10 when allowed to stand at 40° C. for 10 minutes and 30 minutes, respectively;
5. Working in a wide temperature range of from 10 to 65° C. with an optimum temperature being recognized at about 40° C.;
6. Influences of chelating agents: The activity not impeded with ethylenediamine tetraacetic acid (EDTA), ethyleneglycol-bis-(β-aminoethylether) N,N,N',N"-tetraacetic acid (EGTA), N,N-bis(carboxymethyl)glycine (nitrilotriacetic acid) (NTA), sodium tripolyphosphate (STPP) and zeolite;
7. Influences of surface active agents: Undergoing little inhibition of activity by means of surface active agents such as sodium linear alkylbenzenesulfonates (LAS), sodium alkylsulfates (AS), sodium polyoxyethylene alkylsulfates (ES), sodium alpha-olefinsulfonates (AOS), sodium alpha-sulfonated aliphatic acid esters (alpha-SFE), sodium alkylsulfonates (SAS), polyoxyethylene secondary alkyl ethers, fatty acid salts (sodium salts), and dimethyldiallylammonium chloride;
8. Having a strong resistance to proteinases; and
9. Molecular weight (determined by gel chromatography): Having a maximum peak at 180,000±10,000.
10. Preferably such enzyme is obtained by isolation from a culture product of *Bacillus* sp KSM-635.

4) The alkaline bacterial endoglucanases described in EP 271 004A published by Kao on Jun. 15, 1988 are also suitable for the purpose of the present invention. Please refer to the description page 9, line 15 to page 23, line 17 and page 31, line 1 to page 33, line 17 for a detailed description of the enzymes and its production. Those are:

Alkaline Cellulase K-534 from KSM 534, FERM BP 1508,
Alkaline Cellulase K-539 from KSM 539, FERM BP 1509,
Alkaline Cellulase K-577 from KSM 577, FERM BP 1510,
Alkaline Cellulase K-521 from KSM 521, FERM BP 1507,
Alkaline Cellulase K-580 from KSM 580, FERM BP 1511,
Alkaline Cellulase K-588 from KSM 588, FERM BP 1513,
Alkaline Cellulase K-597 from KSM 597, FERM BP 1514,
Alkaline Cellulase K-522 from KSM 522, FERM BP 1512,
Alkaline Cellulase E-II from KSM 522, FERM BP 1512,
Alkaline Cellulase E-III from KSM 522, FERM BP 1512.
Alkaline Cellulase K-344 from KSM 344, FERM BP 1506, and
Alkaline Cellulase K-425 from KSM 425, FERM BP 1505.

Also encompassed in the present invention are variants of the above described enzymes obtained by various techniques known by persons skilled in the art such as directed evolution.

The Oxygen Bleach

As an another essential ingredient, the compositions according to the present invention comprise an oxygen bleach or a mixture thereof.

The oxygen bleach in the composition may come from a variety of sources, such as hydrogen peroxide or any of the addition compounds of hydrogen peroxide, or organic peroxyacid, or mixtures thereof. By addition compounds of hydrogen peroxide, it is meant compounds which are formed by the addition of hydrogen peroxide to a second chemical compound, which may be for example an inorganic salt, urea or organic carboxylate, to provide the addition compound.

Examples of the addition compounds of hydrogen peroxide include inorganic perhydrate salts, the compounds hydrogen peroxide forms with organic carboxylates, urea, and compounds in which hydrogen peroxide is clathrated.

Examples of inorganic perhydrate salts include perborate, percarbonate, perphosphate and persilicate salts. The inorganic perhydrate salts are normally the alkali metal salts. The alkali metal salt of percarbonate, perborate or mixtures thereof, are the preferred inorganic perhydrate salts for use herein. Preferred alkali metal salt of percarbonate is sodium percarbonate.

In a preferred embodiment of the present invention, the oxygen bleach is a peroxygen source, preferably an alkali metal salt of percarbonate, more preferably sodium percarbonate.

Other suitable oxygen bleaches include persulphates, particularly potassium persulphate $K_2S_2O_8$ and sodium persulphate $Na_2S_2O_8$. Examples of inorganic perhydrate salts include perborate, percarbonate, perphosphate and persilicate salts. The inorganic perhydrate salts are normally the alkali metal salts.

The alkali metal percarbonate bleach is usually in the form of the sodium salt. Sodium percarbonate is an addition compound having a formula corresponding to $2Na_2CO_3 3H_2O_2$. To enhance storage stability the percarbonate bleach can be coated with, e.g., a further mixed salt of an alkali metal sulphate and carbonate. Such coatings together with coating processes have previously been described in GB 1466799. The weight ratio of the mixed salt coating material to percarbonate lies in the range from 1:2000 to 1:4, more preferably from 1:99 to 1:9, and most preferably from 1:49 to 1:19. Preferably, the mixed salt is of sodium sulphate and sodium carbonate which has the general formula $Na_2SO_4.n.Na_2CO_3$ wherein n is from 0.1 to 3, preferably n is from 0.3 to 1.0 and most preferably n is from 0.2 to 0.5.

Commercially available carbonate/sulphate coated percarbonate bleach may include a low level of a heavy metal sequestrant such as EDTA, 1-hydroxyethylidene 1,1-diphosphonic acid (HEDP) or an aminophosphonate, that is incorporated during the manufacturing process. Preferred heavy metal sequestrants for incorporation as described herein above include the organic phosphonates and amino alkylene poly(alkylene phosphonates) such as the alkali metal ethane 1-hydroxy diphosphonates, the nitrilo trimethylene phosphonates, the ethylene diamine tetra methylene phosphonates and the diethylene triamine penta methylene phosphonates.

Typically, the compositions of the present invention comprise from 5% to 80% by weight of the total composition of an oxygen bleach or mixtures thereof, preferably from 10% to 70% and more preferably from 15% to 60%.

Preferably, the compositions herein typically contain from 5% to 80%, preferably from 10% to 70% by weight, most preferably from 15% to 60% by weight of an alkali metal percarbonate bleach (when expressed on an AvOx basis of 13.5%) in the form of particles having a mean size from 250 to 900 micrometers, preferably 500 to 700 micrometers.

Available Oxygen (AvO) Content

Oxygen based bleaching agents of the present invention contain "available" oxygen atoms that are ultimately transferred to the target substrate in the oxidation process (AvO). Sources of AvO suitable for the composition of the present invention include peroxygen sources such as sodium percarbonate, sodium perborate monohydrate and sodium perborate tetrahydrate. These are typically formulated with bleach activators and bleach catalysts which mediate the transfer of available oxygen to the target substrate (e.g. soils).

The AvO content of a composition (expressed as a percentage) can be calculated on the basis of its formulated levels of peroxygen sources or determined experimentally using a thiosulfate titration. If the formulated levels of peroxygen source(s) and the percentage AvO of these sources are known, the percentage of Available oxygen (AvO) of the composition can be calculated as shown in the following example involving a bleach additive formulation comprising two peroxygen sources:

Formulated level of Sodium Percarbonate (Solvay S222)=10.6%

% AvO in Sodium Percarbonate Raw Material=14.1%

Formulated level of Sodium Perborate Monohydrate (Degussa)=8.6%

% AvO in Sodium Perborate Monohydrate Raw Material=15.5%

Total AvO in composition=$(10.6/100\times14.1)+(8.6/100\times15.5)=2.82\%$

Where the formulated levels of peroxygen sources (or their AvO content) are not known, the AvO content of the entire composition can be determined using a Method for Measuring Level of Total Available Oxygen (AvO) in a Bleach Composition (see example).

Surfactants

The compositions of the present invention comprise as another essential ingredient surfactants or a mixture thereof.

The compositions will comprise from 0.01% to 20%, preferably from 0.1% to 15% and more preferably from 0.5% to 8% by weight of the total composition of surfactant or a mixture thereof. The presence of surfactants, in such specific amount, is necessary to provide excellent cleaning performance as well as a good physical stability of the composition.

An important feature of the composition of the present invention is the specific weight ratio between the available oxygen (AvO), coming from the oxygen bleach source, and the surfactants. Indeed, according to the present invention, the weight ratio of oxygen bleach source to surfactant must be greater than 0.45. In a preferred embodiment, the weight ratio of oxygen bleach source to surfactant is greater than 1.0, and more preferably greater than 3.0.

Indeed, it is within this specific ratio that the composition of the present invention delivers the best performance benefit in view of the cleaning aspect as well in view of the bleaching performance. It is also this specific ratio that the activity of the enzyme is optimized.

Suitable surfactants for use herein include any nonionic, anionic, zwitterionic, cationic and/or amphoteric surfactants or mixture thereof. Particularly suitable surfactants for use herein are nonionic surfactants such as alkoxylated nonionic surfactants and/or polyhydroxy fatty acid amide surfactants and/or amine oxides and/or zwitterionic surfactants like the zwitterionic betaine surfactants described herein after.

Suitable anionic surfactants include alkyl sulfate surfactant. Preferred alkyl sulfate surfactants include water soluble salts or acids of the formula $ROSO_3M$ wherein R is preferably a $C_{10}$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quarternary ammonium cations derived from alkylamines such as ethylamine, diethylamine, triethylamine, and mixtures thereof, and the like). Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Suitable anionic surfactants include Alkyl Alkoxylated Sulfate Surfactant. Preferred Alkyl Alkoxylated Sulfate Surfactant include water soluble salts or acids of the formula $RO(A)_mSO_3M$ wherein R is an unsubstituted $C_{10}$-$C_{24}$ alkyl or hydroxyalkyl group having a $C_{10}$-$C_{24}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines such as ethylamine, diethylamine, triethylamine, mixtures thereof, and the like.

Exemplary surfactants are $C_{12}$-$C_{18}$ alkyl polyethoxylate (1.0) sulfate; $C_{12}$-$C_{18}E(1.0)M$; $C_{12}$-$C_{18}$ alkyl polyethoxylated (2.25) sulfate; $C_{12}$-$C_{18}E(2.25)M$; $C_{12}$-$C_{18}$ alkyl polyethoxylate(3.0)sulfate $C_{12}$-$C_{18}E(3.0)$, and $C_{12}$-$C_{18}$ alkyl polyethoxylate (4.0) sulfate $C_{12}$-$C_{18}E(4.0)M$, wherein M is conveniently selected from sodium and potassium.

Accordingly suitable other anionic surfactants include salts (including, for example, sodium, potassium, ammonium, and substituted ammonium salts such as mono-, di- and triethanolamine salts) of soap, $C_9$-$C_{20}$ linear alkylbenzenesulphonates, $C_8$-$C_{22}$ primary or secondary alkanesulphonates, $C_8$-$C_{24}$ olefinsulphonates, sulphonated polycarboxylic acids prepared by sulphonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglycoside (the nonionic nonsulfated compounds being described below), branched primary alkyl sulfates, alkyl polyethoxy carboxylates such as those of the formula $RO(CH_2CH_2O)_kCH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred surfactants for use in the compositions according to the present invention are the alkyl sulfates, alkyl alkoxylated sulfates, and mixtures thereof.

Another preferred surfactant system for use in the compositions according to the present invention are acyl sarcosinates surfactants.

Suitable nonionic surfactants include compounds produced by the condensation of alkylene oxide groups (hydrophilic in nature) with an organic hydrophobic compound, which may be aliphatic or alkyl aromatic in nature. The length of the polyoxyalkylene group which is condensed with any particular hydrophobic group can be readily adjusted to yield a water-soluble compound having the desired degree of balance between hydrophilic and hydrophobic elements.

Preferred for use in the present invention are nonionic surfactants such as the polyethylene oxide condensates of alkyl phenols, e.g., the condensation products of alkyl phenols having an alkyl group containing from about 6 to 16 carbon atoms, in either a straight chain or branched chain configuration, with from about 4 to 25 moles of ethylene oxide per mole of alkyl phenol.

Preferred nonionic surfactants are the water-soluble condensation products of aliphatic alcohols containing from 8 to 22 carbon atoms, in either straight chain or branched configuration, with an average of up to 25 moles of ethylene oxide per more of alcohol. Particularly preferred are the condensation products of alcohols having an alkyl group containing from about 9 to 15 carbon atoms with from about 2 to 10 moles of ethylene oxide per mole of alcohol; and condensation products of propylene glycol with ethylene oxide. Most preferred are condensation products of alcohols having an alkyl group containing from about 12 to 15 carbon atoms with an average of about 3 moles of ethylene oxide per mole of alcohol.

The nonionic surfactant system herein can also include a polyhydroxy fatty acid amide component. Polyhydroxy fatty acid amides may be produced by reacting a fatty acid ester and an N-alkyl polyhydroxy amine. The preferred amine for use in the present invention is $N—(R^1)—CH_2(CH_2OH)_4—CH_2—OH$ and the preferred ester is a $C_{12}$-$C_{20}$ fatty acid methyl ester. Most preferred is the reaction product of N-methyl glucamine with $C_{12}$-$C_{20}$ fatty acid methyl ester. Methods of manufacturing polyhydroxy fatty acid amides have been described in WO92 6073, published on 16 Apr., 1992. This application describes the preparation of polyhydroxy fatty acid amides in the presence of solvents. In a highly preferred embodiment of the invention N-methyl glucamine is reacted with a $C_{12}$-$C_{20}$ methyl ester. It also says that the formulator of granular detergent compositions may find it convenient to run the amidation reaction in the presence of solvents which comprise alkoxylated, especially ethoxylated (EO 3-8) $C_{12}$-$C_{14}$ alcohols (page 15, lines 22-27). This directly yields nonionic surfactant systems which are preferred in the present invention, such as those comprising N-methyl glucamide and $C_{12}$-$C_{14}$ alcohols with an average of 3 ethoxylate groups per molecule. Nonionic surfactant systems, and granular detergents made from such systems have been described in WO 92 6160, published on 16 Apr., 1992.

Other suitable surfactants according to the present invention includes also cationic, ampholytic, zwitterionic, and semi-polar surfactants, as well as nonionic surfactants other than those already described herein, including the semi-polar nonionic amine oxides described below.

Cationic detersive surfactants suitable for use in the laundry detergent compositions of the present invention are those having one long-chain hydrocarbyl group. Examples of such cationic surfactants include the ammonium surfactants such as alkyldimethylammonium halogenides, and those surfactants having the formula:

$$[R^2(0R^3)y][R^4(OR^3)y]_2R^5N+X—$$

wherein $R^2$ is an alkyl or alkyl benzyl group having from about 8 to about 18 carbon atoms in the alkyl chain, each $R^3$ is selected from the group consisting of $—CH_2CH_2—$, $—CH_2CH(CH_3)—$, $—CH_2CH(CH_2OH)—$, $—CH_2CH_2CH_2—$, and mixtures thereof; each $R^4$ is selected from the group consisting of $C_1$-$C_4$ alkyl, $C_1$-$C_4$ hydroxyalkyl, benzyl ring structures formed by joining the two $R^4$ groups, $—CH_2COH—CHOHCOR_6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion. Other cationic surfactants useful herein are also described in U.S. Pat. No. 4,228,044, Cambre, issued Oct. 14, 1980, incorporated herein by reference.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched chain. One of the aliphatic substituents contains at least 8 carbon atoms, typically from about 8 to about 18 carbon atoms, and at least one contains an anionic water-solubilizing group e.g. carboxy, sulfonate, sulfate. See U.S. Pat. No. 3,929,678 to Laughlin et al., issued Dec. 30, 1975 at column 19, lines 18-35 (herein incorporated by reference) for examples of ampholytic surfactants.

Zwitterionic surfactants are also suitable for use in laundry detergent compositions. These surfactants can be broadly described as derivatives of secondary and tertiary amines, derivates of heterocyclic secondary and tertiary amines, or derivatives of quaternary ammonium, quarternary phosphonium or tertiary sulfonium compounds. See U.S. Pat. No. 3,929,678 to Laughlin et al., issued Dec. 30, 1975 at columns 19, line 38 through column 22, line 48 (herein incorporated by reference) for examples of zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing form about 1 to about 3 carbon atoms; water-soluble phosphine oxides containing one alkyl moiety of form about 10 to about 18 carbon atoms and 2 moieties selected form the group consisting of alkyl groups and hydroxyalkyl groups containing from about 1 to about 3 carbon atoms. Semi-polar nonionic detergent surfactants include the amine oxide surfactants having the formula $R^3(OR^4)_xNO(R^5)_2$ Optional Ingredients The compositions herein may further comprise a variety of other optional ingredients such as bleach activators, filers, chelating agents, radical scavengers, antioxidants, stabilisers, builders, soil suspending polymer, polymeric soil release agents, dye transfer inhibitor, solvents, suds controlling agents, suds booster, brighteners, perfumes, pigments, dyes and the like.

Bleach Activators

Typically to overcome poor bleaching performance of hydrogen peroxide alone, persalt bleaches are formulated in granular compositions with so-called bleach activators. The bleach activators are species that react with hydrogen peroxide to form a peroxyacid or peracid. Typically, the compositions of the present invention might comprise from 1% to 30% by weight of the total composition of a bleach activators, preferably from 2% to 20% and more preferably from 3% to 10%.

The bleaching mechanism generally, and the surface bleaching mechanism in particular, in the washing solution are not completely understood. While not intending to be limited by theory, however, it is believed that the bleach activator undergoes nucleophilic attack by a perhydroxide anion, for example from aqueous hydrogen peroxide, to form a percarboxylic acid. This reaction is commonly referenced in the art as perhydrolysis.

A second species present in the washing solution is the diacylperoxide (also referred to herein as "DAP"). It is imperative that some DAP production is present in order to improve bleaching of specific stains such as, for example, those stains caused by spaghetti sauce or barbecue sauce. The peroxyacid acids are particularly useful for removing dingy soils from textiles. As used herein, "dingy soils" are those which have built up on textiles after numerous cycles of usage and washing and thus, cause the white textile to have a gray or yellow tint. Accordingly, the bleaching mechanism herein preferably produces an effective amount of peroxyacid and DAP to bleach both dingy stains as well as stains resulting from spaghetti and the like.

Further, it is believed that bleach activators within the scope of the invention render the peroxygen bleaches more efficient even at bleach solution temperatures wherein the bleach activators are not necessary to activate the bleach, for example at temperatures above 60° C. As a consequence, less peroxygen bleach is required to obtain the same level of surface bleaching performance as compared with peroxygen bleach alone.

Examples of suitable compounds of this type are disclosed in British Patent GB1586769 and GB2143231. Examples of such compounds are tetracetyl ethylene diamine, (TAED), sodium 3, 5, 5 trimethyl hexanoyloxybenzene sulphonate, diperoxy dodecanoic acid as described for instance in U.S. Pat. No. 4,818,425 and nonylamide of peroxyadipic acid as described for instance in U.S. Pat. No. 4,259,201 and n-nonanoyloxybenzenesulphonate (NOBS), and acetyl triethyl citrate (ATC) such as described in European patent application 91870207.7. Preferred example are also N-acyl caprolactam selected from the group consisting of substituted or unsubstituted benzoyl caprolactam, octanyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam. The compositions herein may comprise mixtures of said bleach activators.

Preferred mixtures of bleach activators herein comprise n-nonanoyloxybenzene-sulphonate (NOBS) together with a second bleach activator having a low tendency to generate diacyl peroxide, but which delivers mainly peracid. Said second bleach activators may include tetracetyl ethylene diamine (TAED), acetyl triethyl citrate (ATC), acetyl caprolactam, benzoyl caprolactam and the like, or mixtures thereof. Indeed, it has been found that mixtures of bleach activators comprising n-nonanoyloxybenzene-sulphonate and said second bleach activators, contribute to further boost particulate soil removal performance while exhibiting at the same time good performance on diacyl peroxide sensitive soil (e.g., beta-carotene) and on peracid sensitive soil (e.g., body soils).

In a preferred embodiment, the bleach activator used in the liquid bleach composition has the general formula:

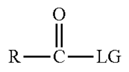

wherein R is an alkyl group, linear or branched, containing from about 1 to 11 carbon atoms and LG is a suitable leaving group. As used herein, a "leaving group" is any group that is displaced from the bleach activator as consequence of nucleophilic attack on the bleach activator by the perhydroxide anion, i.e. perhydrolysis reaction.

Generally, a suitable leaving group is electrophilic and is stable such that the rate of the reverse reaction is negligible. This facilitates the nucleophilic attack by the perhydroxide anion. The leaving group must also be sufficiently reactive for the reaction to occur within the optimum time frame, for example during the wash cycle. However, if the leaving group is too reactive, the bleach activator will be difficult to stabilize. In the past, those skilled in the art have not been successful in formulating an aqueous liquid bleach having the desired stability for a practical shelf-life.

These characteristics are generally paralleled by the pKa of the conjugate acid of the leaving group, although exceptions to this convention are known. The conjugate acid of the leaving group in accordance with the present invention preferably has a pKa in a range from about 4 to about 13, more preferably from about 6 to about 11, and most preferably from about 8 to about 11.

Preferably, the leaving group has the formula:

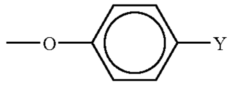

wherein Y is selected from the group consisting of $SO_3^-M^+$, $COO^-M^+$, $SO_4^-M^+$, $PO_4^-M^+$, $PO_3^-M^+$. $(N^+R^2_3)X^-$ and $O \rightarrow N(R^2_2)$, M is a cation and X is an anion, both of which provide solubility to the bleach activator, and $R^2$ is an alkyl chain containing from about 1 to about 4 carbon atoms or H. In accordance with the present invention, M is preferably an alkali metal, with sodium being most preferred. Preferably, X is a hydroxide, methylsulfate or acetate anion.

Other suitable leaving groups have the following formulas

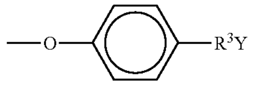

or

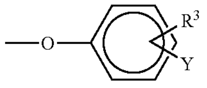

wherein Y is the same as described above and $R^3$ is an alkyl chain containing from about 1 to about 8 carbon atoms, H or $R^2$.

While numerous bleach activators as described above are suitable for use in the present liquid bleach composition, a preferred bleach activator has the formula:

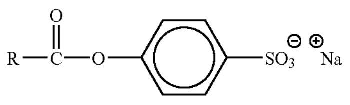

wherein R is an alkyl chain, linear or branched, containing from 1 to 11 carbon atoms. More preferably, R is an alkyl chain, linear or branched, containing from 3 to 11, even more preferably from 8 to 11.

Most preferably, the bleach activator has the formula:

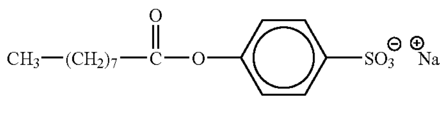

which is also referred to as sodium n-nonyloxybenzene sulfonate (hereinafter referred to as "NOBS"). This bleach activator and those described previously may be readily synthesized by well known reaction schemes or purchased commercially, neither of which is more preferred. Those skilled in the art will appreciate that other bleach activators beyond those described herein which are readily water-soluble can be used in the present bleach composition without departing from the scope of the invention.

Fillers

The compositions of the present invention may comprise a filler salt as a highly preferred though option ingredient. Suitable filler salts herein are selected from the group consisting of sodium sulfate, sodium chloride, sodium tripolyphosphate "STPP" and the like. Typically, the compositions according to the present invention may comprise from up to 75% by weight of the total composition of a filler salt or a mixture thereof, preferably from 70% to 10% and more preferably from 60% to 30%.

Chelating Agents

The compositions of the present invention may comprise a chelating agent as an optional ingredient. Typically, the compositions according to the present invention comprise up to 5% by weight of the total composition of a chelating agent, or mixtures thereof, preferably from 0.01% to 1.5% by weight and more preferably from 0.01% to 0.5%.

Suitable phosphonate chelating agents for use herein may include alkali metal ethane 1-hydroxy diphosphonates (HEDP), alkylene poly(alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®. Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene. A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins.

Ethylenediamine N,N'-disuccinic acids is, for instance, commercially available under the tradename ssEDDS® from Palmer Research Laboratories.

Suitable amino carboxylates to be used herein include ethylene diamine tetra acetates, diethylene triamine pentaacetates, diethylene triamine pentaacetate (DTPA),N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents to be used herein include salicylic acid, aspartic acid, glutamic acid, glycine, malonic acid or mixtures thereof. Particularly preferred chelating agents to be used herein are amino aminotri(methylene phosphonic acid), di-ethylene-triamino-pentaacetic acid, diethylene triamine penta methylene phosphonate, 1-hydroxy ethane diphosphonate, ethylenediamine N,N'-disuccinic acid, and mixtures thereof.

Anti-Redeposition Polymer

The compositions according to the present invention may further comprise an anti-redeposition polymer or mixtures thereof, as an optional ingredient.

Suitable anti-redeposition polymers include polymeric polycarboxylates and: polyacrylates polymers, preferably having a weight average molecular weight of from 1,000 Da to 20,000 Da. Suitable anti-redeposition polymers include also co-polymers of maleic acid and acrylic acid, preferably having a molar ratio of maleic acid monomers to acrylic acid monomers of from 1:1 to 1:10 and a weight average molecular weight of from 10,000 Da to 200,000 Da, or preferably having a molar ratio of maleic acid monomers to acrylic acid monomers of from 0.3:1 to 3:1 and a weight average molecular weight of from 1,000 Da to 50,000 Da. Suitable polycarboxylates are the Sokalan CP, PA and HP ranges (BASF) such as Sokalan CP5, PA40 and HP22, and the Alcosperse range of polymers (Alco) such as Alcosperse 725, 747, 408, 412 and 420.

Further suitable anti-redeposition polymers include cellulose derivatives, for example carboxymethyl cellulose, methylhydroxyethyl cellulose, and mixtures thereof. An example of a suitable carboxymethylcellulose is Finnfix® BDA, supplied by CPKelco, Arhem, Netherlands. An example of a suitable methylhydroxymethyl cellulose is Tylose® MH50 G4, supplied by SE Tylose GmbH, Wiesbaden, Germany.

Further suitable anti-redeposition polymers include polyamine polymers known to those skilled in the art. Particularly suitable polyamine polymers for use herein are polyalkoxylated polyamines.

Typically, the compositions comprise up to 10% by weight of the total composition of such a soil suspending polyamine polymer or mixtures thereof, preferably from 0.1% to 5% and more preferably from 0.3% to 2%.

The compositions herein may also comprise other polymeric soil release agents known to those skilled in the art. Such polymeric soil release agents are characterised by having both hydrophilic segments, to hydrophilize the surface of hydrophobic fibres, such as polyester and nylon, and hydrophobic segments, to deposit upon hydrophobic fibres and remain adhered thereto through completion of washing and rinsing cycles and, thus, serve as an anchor for the hydrophilic segments. This can enable stains occurring subsequent to treatment with the soil release agent to be more easily cleaned in later washing procedures.

If utilized, soil release agents will generally comprise from 0.01% to 10.0%, by weight, of the compositions herein, typically from 0.1% to 5%, preferably from 0.2% to 3.0%.

Dye Transfer Inhibitor

The compositions of the present invention may also include one or more materials effective for inhibiting the transfer of dyes from one dyed surface to another during the cleaning process. Generally, such dye transfer inhibiting agents include polyvinyl pyrrolidone polymers, polyamine N-oxide polymers, co-polymers of N-vinylpyrrolidone and N-vinylimidazole, manganese phthalocyanine, peroxidases, and mixtures thereof. If used, these agents typically comprise from 0.01% to 10% by weight of the composition, preferably from 0.01% to 5%, and more preferably from 0.05% to 2%.

Brightener

Any optical brighteners, fluorescent whitening agents or other brightening or whitening agents known in the art can be incorporated in the instant compositions when they are designed for fabric treatment or laundering, at levels typically from about 0.05% to about 1.2%, by weight, of the compositions herein.

Processes of Treating Fabrics

The present invention encompasses a process of treating fabrics which comprises the steps of forming an aqueous bath comprising water, a conventional laundry detergent, preferably a granular laundry detergent, and a particulate bleach additive composition according to the present invention, and subsequently contacting said fabrics with said aqueous bath.

The processes of treating, preferably bleaching, fabrics according to the present invention delivers effective whiteness performance as well as effective stain removal and stain release performance. The term 'stain release' refers to the ability of the composition to modify the surfaces of the textile over multiple wash cycles resulting in reduced adhesion of soils.

The process of treating fabrics herein comprises the steps of forming an aqueous bath comprising water, a conventional laundry detergent and a particulate bleach additive composition, as described herein, subsequently contacting said fabrics with said aqueous bath.

By "conventional laundry detergent" it is meant herein, a laundry detergent composition currently available on the market. Preferably, said conventional laundry detergent comprises at least one surfactant. Said laundry detergent compositions may be formulated as particulates (including powders, pearls, granules, tablets and the like), liquids (liquids, gels, and the like) as well as detergent forms based on water-soluble or water-permeable pouches comprising liquids and/or particulates (such as liquid-tabs). Suitable particulate laundry detergent compositions are for example DASH Powder®, ARIEL Tablets®, ARIEL® powdery and other products sold under the trade names ARIEL® or TIDE®.

In a preferred embodiment herein, the conventional laundry detergent is a conventional particulate laundry detergent more preferably a conventional powder, pearl, granule or tablet laundry detergent.

In a preferred embodiment according to the present invention, the conventional laundry detergent as described herein and, the particulate bleach additive composition herein are dissolved or dispersed, preferably substantially dissolved or dispersed, in the aqueous bath formed in the process according to the present invention. By "substantially dissolved or dispersed" it is meant herein, that at least 50%, preferably at least 80%, more preferably at least 90%, even more preferably at least 95%, still more preferably at least 98%, and most preferably at least 99%, of said conventional laundry detergent and/or said particulate bleach additive composition are dissolved or dispersed in the aqueous bath formed in the process according to the present invention.

The particulate bleach additive composition and the conventional detergent composition may be delivered into the washing machine either by charging the dispenser drawer of the washing machine with one or both of the detergents or by directly charging the drum of the washing machine with one or both of the detergents. More preferably the particulate bleach additive composition is directly placed into the drum of the washing machine, preferably using a dosing device, such as a dosing ball (such as the Vizirette®. Even more preferably the particulate bleach additive composition and the conventional detergent composition are both placed into the drum of the washing machine, preferably using suitable dosing devices such as dosing balls, dosing nets etc. The particulate bleach additive composition is preferably delivered to the main wash cycle of the washing machine before, but more preferably at the same time as the conventional detergent composition.

During the processes according to the present invention the particulate bleach additive compositions herein is typically used in dissolved form. By "in dissolved form", it is meant herein that the particulate bleach additive compositions according to the present invention may be dissolved by the user, preferably in water. The dissolution occurs in a washing machine. Said compositions can be dissolved up to 500 times its own weight, preferably from 5 to 350 times and more preferably from 10 to 200 times.

Packaging Form of the Particulate Compositions:

Depending on the end-use envisioned, the compositions herein can be packaged in a variety of containers including conventional boxes, tubs etc.

EXAMPLES

1—Method for Measuring Level of Total Available Oxygen (AvO) in Particulate Bleach Composition 2 L of water (on a beaker) is placed on a stirrer hotplate. The particulate bleach composition (8 g of product) is added and dispersed through the solution. The temperature is maintain at 20° C. Samples are taken from the solution at 2 minutes time intervals for 20 minutes and are titrated by the "titration procedure" described below to determine the level of available oxygen (AvO) at each point.

Titration Procedure

An aliquot of the detergent solution (above) and 2 ml sulphuric acid are added into the beaker. About 0.2 g of ammonium molybdate catalyst (tetrahydrate form) are added. Then, 3 mL of 10% sodium iodide solution are added.

Titration with sodium thiosulfate is conducted by adding soluble starch when the yellow colour is becoming faint, turning the solution blue. More thiosulfate is added until the end point is reached (blue starch complex is decolourised).

The level of AvO, measured in units of percentage available oxygen by weight, for the sample at each time interval corresponds to the amount of titre according to the following equation:

$$AvO = \frac{Vol\ S_2O_3\ (\text{ml})}{1} \times \text{Molarity} \times \frac{1}{2} \times \frac{16}{1} \times \frac{1}{\text{sample mass (g)}}$$

2—Method for Evaluating Bleaching Performances of Particulate Bleach Compositions Bleaching performances are evaluated on soiled fabric under additive-conditions (also referred herein as "through-the-wash" conditions). The particulate bleach additive composition is added together with a conventional particulate laundry detergent (such as DASH powder, TIDE®, ARIEL® tablets, ARIEL® powder). The particulate bleach additive composition is dosed at 30 grams per wash-load and the conventional laundry detergent is dosed at 110 grams per wash load for granules and two tabs per wash load for tablets (recommended dosages). In the washing machine, the soiled fabrics are washed according to the standard procedure of the washing machine at a temperature of from 30° to 70° C. for 10 to 100 minutes and then rinsed. Soiled fabrics/swatches (with for example tea, coffee stains) are commercially available from Warwick Equest Ltd., Stanley, Co. (UK).

A visual grading are used to assign difference in panel units (psu) in a range from 0 to 4, wherein 0 means no noticeable difference in bleaching performance between a particulate bleach additive composition according to the present invention and a reference composition and 4 means a noticeable difference in bleaching performance between a particulate bleach additive composition according to the present invention and a reference composition.

3—Compositions

The following examples further illustrate the present invention. The compositions are made by combining the listed ingredients in the listed proportions (weight % active material except in the case of Mannanase, Protease and Cellulase which refers to the % of enzyme granulate). The following Examples are meant to exemplify compositions according to the present invention but are not necessarily used to limit or otherwise define the scope of the present invention.

All compositions I to V exhibit excellent bleaching and cleaning performances as well as fabric safety.

| Ingredient | I | II | III | IV | V |
|---|---|---|---|---|---|
| Sodium percarbonate | 33.0 | 54.0 | 18.0 | 53.0 | 33.0 |
| TAED | 15.0 | 0.30 | 4.4 | — | — |
| Polyamine polymer | 6.0 | — | — | — | 6.0 |
| Acrylic Acid/Maleic Acid Copolymer | 2.0 | — | — | 1.3 | — |
| HEDP | 1.3 | — | 1.2 | 0.7 | — |
| Carboxymethyl cellulose | — | 0.1 | 0.5 | — | — |
| Polyvinylpyrrolidone (PVP) | — | 0.2 | 0.1 | — | — |
| Anionic (LAS) surfactant | 1.2 | 4.5 | 3.7 | 7.0 | — |
| Nonionic (AE7) surfactant | 0.5 | 1.0 | 0.4 | 2.0 | 0.1 |
| Sodium lauroyl sarcosinate surfactant | — | 1.0 | — | — | — |
| Sodium xylene sulfonate (hydrotrope) | — | 1.1 | — | — | — |
| Mannanase granulate | 0.2 | — | 0.1 | 0.1 | — |

-continued

| Ingredient | I | II | III | IV | V |
|---|---|---|---|---|---|
| Protease granulate | — | 0.5 | 0.1 | 0.2 | — |
| Cellulase granulate | 0.2 | 0.2 | 0.1 | 0.4 | 0.1 |
| Brightener | 0.1 | — | 0.07 | 0.12 | — |
| Soil release agent | — | — | 0.56 | 0.3 | — |
| Sodium carbonate | Balance | Balance | Balance | Balance | Balance |
| AvO % | 3.50 | 5.72 | 1.91 | 5.61 | 3.50 |
| Total Surfactant Level % | 1.70 | 6.50 | 4.10 | 9.0 | 0.1 |
| Ratio AvO/Surfactant | 2.06 | 0.88 | 0.47 | 0.62 | 35 |

Sodium percarbonate is S222 available from Solvay.

TAED is tetraacetylethylenediamine, Peractive ®, available from Clariant GmbH.

Polyamine polymer is bis($(C_2H_5O)(C_2H_4O)_n$)($CH_3$)—$N^+$—$C_xH_{2x}$—$N^+$—($CH_3$)-bis($(C_2H_5O)(C_2H_4O)_n$), wherein n = from 20 to 30, and x = from 3 to 8.

Acrylic acid/maleic acid copolymer is an acrylate/maleate copolymer with a ratio 70:30 and molecular weight of 70000, available from BASF.

HEDP is hydroxyethane diphosphonate available from Dow Chemical.

Carboxymethyl cellulose is Finnfix ® GDA available from CPKelco, (NL).

Polyvinylpyrrolidone is PVP-K15 available from ISP Corporation (NJ, USA).

Anionic (LAS) is sodium alkylbenzenesulfonate having an average aliphatic carbon chain length $C_{11}$-$C_{12}$ available from Stepan (USA).

Nonionic (AE7) is $C_{12}$-$C_{15}$ alcohol ethoxylate, with an average degree of ethoxylation of 7, available from Huntsman, (Utah, USA).

Sodium lauroyl sarcosinate is Hamposyl L95, available from Chattern Chemicals, (Tennessee, USA).

Sodium xylene sulfonate is available from Stepan, (Illinois, USA).

Mannanase granulate is Mannaway available from Novozymes (Denmark) and contains 4 mg active enzyme per gram.

Protease granulate is Savinase, available from Novozymes (Denmark) and contains 15.8 mg active enzyme per gram.

Cellulase granulate is Celluclean, available from Novozymes (Denmark) and contains 15.6 mg active enzyme per gram.

Brightener is Tinopal ® CBS-X available from Ciba Specialty Chemicals, (Switzerland).

Soil release agent is Repel-o-tex ® SF2, available from Rhodia (France).

Sodium carbonate is available from Solvay.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A particulate bleaching composition comprising, based on total composition weight:

a) from about 5% to about 80% of an oxygen bleach;

b) from about 0.01% to about 20% of a surfactant;

c) and from about 0.00005% to about 0.3% of an enzyme wherein said enzyme:

i. exhibits endo-beta-1,4-glucanase activity (E.C. 3.2.1.4); and ii. exhibits greater than 80% of maximum activity at pH 9.2 when measured at 40° C.; and iii. does not comprise a Class A Carbohydrate Binding Module (CBM); wherein the weight ratio of available oxygen (AvO) to surfactant is greater than 0.45.

2. The composition according to claim 1 wherein the enzyme is a bacterial alkaline enzyme exhibiting endo-beta-1,4-glucanase activity (E.C. 3.2.1.4).

3. The composition according to claim 2 wherein the enzyme is a bacterial polypeptide endogenous to a member of the genus *Bacillus*.

4. The composition according to claim 2 wherein the enzyme is a polypeptide containing (i) at least one family 17 carbohydrate binding module and/or (ii) at least one family 28 carbohydrate binding module.

5. The composition according to claim 2 wherein the enzyme is selected from the group consisting of:

(i) an endoglucanase having the amino acid sequence of positions 1 to position 773 of SEQ ID NO:1;

(ii) an endoglucanase having at least 90% sequence identity to the amino acid sequence of position 1 to position 773 of SEQ ID NO:1; or a fragment thereof that has endo-beta-1,4-glucanase activity, when identity is determined by GAP provided in the GCG program using a GAP creation penalty of 3.0 and GAP extension penalty of 0.1; and (iii) mixtures thereof.

6. The composition according to claim 1 wherein said composition comprises from about 0.00005% to about 0.15% by weight of pure enzyme.

7. The composition according to claim 1 comprising, based on total composition weight, from about 10% to about 80% oxygen bleach.

8. The composition according to claim 1 wherein said oxygen bleach comprises a peroxygen source.

9. The composition according to claim 8 wherein said peroxygen source comprises an alkali metal salt of percarbonate.

10. The composition according to claim 9 wherein said alkali metal salt of percarbonate comprises sodium percarbonate.

11. The composition according to claim 1 wherein said surfactant system comprises a material selected from the group consisting of selected from a non-ionic surfactant, an anionic surfactant, a zwitterionic surfactant, a cationic surfactant, an amphoteric surfactant and mixtures thereof.

12. The composition according to claim 1 wherein said surfactant comprises an acyl sarcosinate surfactant.

13. The composition according to claim 1 further comprising, based on total composition weight, up to 30% of a bleach activator.

14. The composition according to claim 13 wherein said bleach activator has the formula:

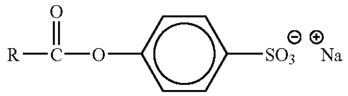

wherein R is a linear or branched alkyl chain, comprising from 1 to 11 carbon atoms.

* * * * *

SEQUENCE LISTING

<160> NUMBER OF SEQ ID NOS: 2

<210> SEQ ID NO 1
<211> LENGTH: 773
<212> TYPE: PRT
<213> ORGANISM: Bacillus sp.

<400> SEQUENCE: 1

Ala Glu Gly Asn Thr Arg Glu Asp Asn Phe Lys His Leu Leu Gly Asn
1 5 10 15

Asp Asn Val Lys Arg Pro Ser Glu Ala Gly Ala Leu Gln Leu Gln Glu
20 25 30

Val Asp Gly Gln Met Thr Leu Val Asp Gln His Gly Glu Lys Ile Gln
35 40 45

Leu Arg Gly Met Ser Thr His Gly Leu Gln Trp Phe Pro Glu Ile Leu
50 55 60

Asn Asp Asn Ala Tyr Lys Ala Leu Ala Asn Asp Trp Glu Ser Asn Met
65 70 75 80

Ile Arg Leu Ala Met Tyr Val Gly Glu Asn Gly Tyr Ala Ser Asn Pro
85 90 95

Glu Leu Ile Lys Ser Arg Val Ile Lys Gly Ile Asp Leu Ala Ile Glu
100 105 110

Asn Asp Met Tyr Val Ile Val Asp Trp His Val His Ala Pro Gly Asp
115 120 125

Pro Arg Asp Pro Val Tyr Ala Gly Ala Glu Asp Phe Phe Arg Asp Ile
130 135 140

Ala Ala Leu Tyr Pro Asn Asn Pro His Ile Ile Tyr Glu Leu Ala Asn
145 150 155 160

```
Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
    370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
            420                 425                 430

Asp Gly Trp Gly Lys Ser Val Asp Ile Leu Gly Ala Glu Lys Leu Thr
        435                 440                 445

Met Asp Val Ile Val Asp Glu Pro Thr Thr Val Ala Ile Ala Ala Ile
    450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
    530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590
```

```
Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Glu
    770


<210> SEQ ID NO 2
<211> LENGTH: 824
<212> TYPE: PRT
<213> ORGANISM: Bacillus sp. KSM-S237

<400> SEQUENCE: 2

Met Met Leu Arg Lys Lys Thr Lys Gln Leu Ile Ser Ser Ile Leu Ile
1               5                   10                  15

Leu Val Leu Leu Leu Ser Leu Phe Pro Ala Ala Leu Ala Ala Glu Gly
            20                  25                  30

Asn Thr Arg Glu Asp Asn Phe Lys His Leu Leu Gly Asn Asp Asn Val
        35                  40                  45

Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

Ala Tyr Lys Ala Leu Ser Asn Asp Trp Asp Ser Asn Met Ile Arg Leu
            100                 105                 110

Ala Met Tyr Val Gly Glu Asn Gly Tyr Ala Thr Asn Pro Glu Leu Ile
        115                 120                 125

Lys Gln Arg Val Ile Asp Gly Ile Glu Leu Ala Ile Glu Asn Asp Met
    130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
                165                 170                 175

Tyr Pro Asn Asn Pro His Ile Ile Tyr Glu Leu Ala Asn Glu Pro Ser
            180                 185                 190
```

-continued

```
Ser Asn Asn Asn Gly Gly Ala Gly Ile Pro Asn Asn Glu Glu Gly Trp
        195                 200                 205

Lys Ala Val Lys Glu Tyr Ala Asp Pro Ile Val Glu Met Leu Arg Lys
    210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Ser Glu Thr Pro Asn Ser Glu Arg Gly Asn Val Met
        275                 280                 285

Ser Asn Thr Arg Tyr Ala Leu Glu Asn Gly Val Ala Val Phe Ala Thr
    290                 295                 300

Glu Trp Gly Thr Ser Gln Ala Ser Gly Asp Gly Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Asn Leu Asp Pro Gly Pro
        355                 360                 365

Asp His Val Trp Ala Pro Glu Glu Leu Ser Leu Ser Gly Glu Tyr Val
    370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
            420                 425                 430

Glu Asn Asn Thr Leu Lys Val Ser Gly Leu Asp Val Ser Asn Asp Val
        435                 440                 445

Ser Asp Gly Asn Phe Trp Ala Asn Ala Arg Leu Ser Ala Asn Gly Trp
    450                 455                 460

Gly Lys Ser Val Asp Ile Leu Gly Ala Glu Lys Leu Thr Met Asp Val
465                 470                 475                 480

Ile Val Asp Glu Pro Thr Thr Val Ala Ile Ala Ala Ile Pro Gln Ser
                485                 490                 495

Ser Lys Ser Gly Trp Ala Asn Pro Glu Arg Ala Val Arg Val Asn Ala
            500                 505                 510

Glu Asp Phe Val Gln Gln Thr Asp Gly Lys Tyr Lys Ala Gly Leu Thr
        515                 520                 525

Ile Thr Gly Glu Asp Ala Pro Asn Leu Lys Asn Ile Ala Phe His Glu
    530                 535                 540

Glu Asp Asn Asn Met Asn Asn Ile Ile Leu Phe Val Gly Thr Asp Ala
545                 550                 555                 560

Ala Asp Val Ile Tyr Leu Asp Asn Ile Lys Val Ile Gly Thr Glu Val
                565                 570                 575

Glu Ile Pro Val Val His Asp Pro Lys Gly Glu Ala Val Leu Pro Ser
            580                 585                 590

Val Phe Glu Asp Gly Thr Arg Gln Gly Trp Asp Trp Ala Gly Glu Ser
        595                 600                 605
```

-continued

```
Gly Val Lys Thr Ala Leu Thr Ile Glu Glu Ala Asn Gly Ser Asn Ala
    610                 615                 620

Leu Ser Trp Glu Phe Gly Tyr Pro Glu Val Lys Pro Ser Asp Asn Trp
625                 630                 635                 640

Ala Thr Ala Pro Arg Leu Asp Phe Trp Lys Ser Asp Leu Val Arg Gly
                645                 650                 655

Glu Asn Asp Tyr Val Ala Phe Asp Phe Tyr Leu Asp Pro Val Arg Ala
            660                 665                 670

Thr Glu Gly Ala Met Asn Ile Asn Leu Val Phe Gln Pro Pro Thr Asn
        675                 680                 685

Gly Tyr Trp Val Gln Ala Pro Lys Thr Tyr Thr Ile Asn Phe Asp Glu
    690                 695                 700

Leu Glu Glu Ala Asn Gln Val Asn Gly Leu Tyr His Tyr Glu Val Lys
705                 710                 715                 720

Ile Asn Val Arg Asp Ile Thr Asn Ile Gln Asp Asp Thr Leu Leu Arg
                725                 730                 735

Asn Met Met Ile Ile Phe Ala Asp Val Glu Ser Asp Phe Ala Gly Arg
            740                 745                 750

Val Phe Val Asp Asn Val Arg Phe Glu Gly Ala Ala Thr Thr Glu Pro
        755                 760                 765

Val Glu Pro Glu Pro Val Asp Pro Gly Glu Glu Thr Pro Pro Val Asp
    770                 775                 780

Glu Lys Glu Ala Lys Lys Glu Gln Lys Glu Ala Glu Lys Glu Glu Lys
785                 790                 795                 800

Glu Ala Val Lys Glu Glu Lys Lys Glu Ala Lys Glu Glu Lys Lys Ala
                805                 810                 815

Val Lys Asn Glu Ala Lys Lys Lys
            820
```